United States Patent [19]

Sellers et al.

[11] 4,246,785
[45] Jan. 27, 1981

[54] TESTING EFFECTIVENESS OF THERMAL INSULATION

[76] Inventors: Gregory J. Sellers, 320 South St., Apartment 14A, Morristown, N.J. 07960; Gerald R. Bretts, 6 Tanglewood Dr., Livingston, N.J. 07039

[21] Appl. No.: 15,930

[22] Filed: Feb. 28, 1979

[51] Int. Cl.³ .............................................. G01K 11/16
[52] U.S. Cl. .................................... 73/356; 73/15 A; 73/343 R
[58] Field of Search ................... 73/356, 358; 116/217

[56] References Cited

U.S. PATENT DOCUMENTS

| | | | |
|---|---|---|---|
| 1,623,666 | 4/1927 | Ferkel | 73/366 |
| 2,172,229 | 9/1939 | Waldo | 73/15 A |
| 2,662,018 | 12/1953 | Smith | 116/217 |
| 2,799,167 | 7/1957 | Loconti | 73/356 |
| 3,274,579 | 9/1966 | Fuller, Jr. | 73/358 X |
| 3,597,976 | 8/1971 | Fryer | 73/358 |
| 3,845,662 | 11/1974 | Surgina et al. | 116/217 X |
| 3,859,856 | 1/1975 | Keele et al. | 73/356 |
| 3,987,660 | 10/1976 | Pelanne | 73/15 A |
| 3,998,098 | 12/1976 | Chilton | 73/356 |
| 4,051,728 | 10/1977 | Metz | 73/343 R |
| 4,070,912 | 1/1978 | McNaughtan | 73/356 |
| 4,095,454 | 6/1978 | Fisher | 73/15 A |
| 4,140,016 | 2/1979 | Fergason | 73/356 |

*Primary Examiner*—Daniel M. Yasich

[57] ABSTRACT

The effectiveness of thermal insulation of barriers, such as walls, floors, or ceilings of a residence, is assessed by measuring the effective values of insulation or R values, of thermal barriers. Suitable devices and procedures for utilizing such devices are provided. The R values so measured can be compared with those suggested for economic insulation in such sources as government publications to determine the desirability of augmenting existing insulation.

The device comprises a holder and a temperature sensor and indicator means supported on a support slidably mounted in the holder. In one embodiment, a single device combines measurement of thermal insulation and comparison with suggested values for economic insulation. A direct measurement of whether installed insulation is adequate is thus provided.

6 Claims, 5 Drawing Figures

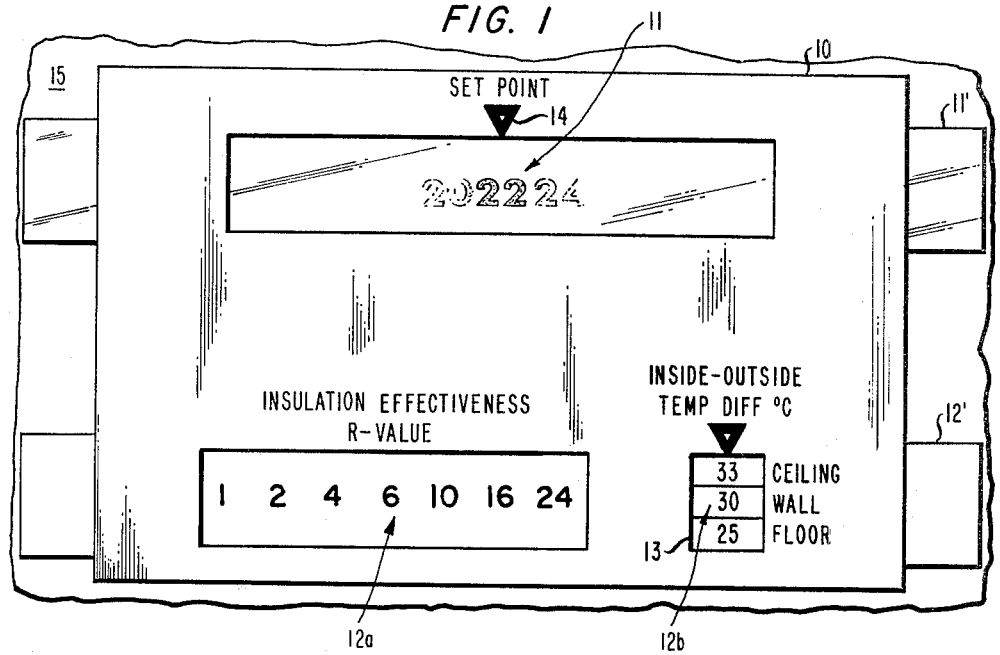
FIG. 1
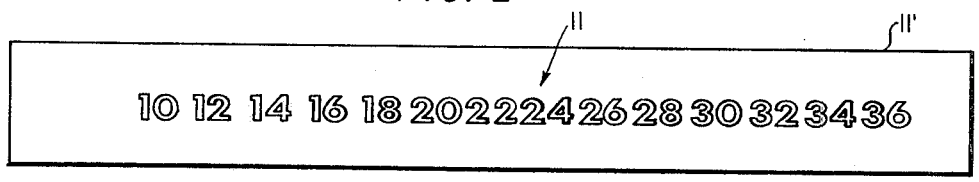
FIG. 2
FIG. 3

TESTING EFFECTIVENESS OF THERMAL INSULATION

BACKGROUND OF THE INVENTION

1. Field of the Invention

The invention is directed to determining the effectiveness and sufficiency of thermal insulation in barriers such as walls, floors, and ceilings.

2. Description of the Prior Art

Heat flows between the interior of residential structures and the exterior by means of conduction, convection and radiation. Heat loss from the structure during the heating season and heat gain during the air conditioning season are economically and physiologically undesirable. This flow is impeded by the addition of thermal insulation placed between the inner and outer walls, in the ceilings above the heated space, and, occasionally, in the floors under it.

Many of the residential dwellings in the United States have less insulation than that considered economically desirable at the current cost of heating or cooling, or have gaps in the existant insulation at various locations, e.g., around windows. It would be desirable for the owners of such dwellings to be able to identify such locations of missing insulation, or to assess the efficacy of that insulation which is present. From such a survey, the owner can determine the need for adding insulation to reduce heat flow.

Several measurement devices exist for assessing the performance of installed residential insulation. These devices typically work on one of two principles. The first type is a heat flow meter in which two termperature-sensitive elements are placed on either side of a suitable, known thermal resistance. This assembly is placed in contact with the surface to be measured, and the temperature difference across the known thermal resistance is measured by means of electrical or electronic circuitry. The heat flow through the known resistance, and hence, through the surface whose heat flow is to be measured is, therefore, determined. A practical equipment for this measurement is marketed under the name of Model HA-100 HEATPROBE® System by International Thermal Instrument Company, Del Mar, Calif. The complexity and precision of this equipment would not make it suitable for individual residential ownership or use. Hence, the cost of its use by a suitably trained individual would inhibit its widespread application.

The second type of equipment usable for insulation performance survey makes use of the fact that any object warmer than absolute zero temperature emits radiation whose quantity is dependent on its temperature and emissivity. A number of sensors of this radiation are in existence, and when coupled with a suitable optical system and electronic amplification, a two-dimensional optical "picture" of the temperature distribution of the surface can be obtained. A practical equipment for this measurement is marketed under the name of AGA THERMOVISION® Systems by AGA Corporation, Secaucus, N.J. This equipment is also complex and costly, and would, therefore, be used only by a trained individual.

A need remains for an inexpensive, easily usable device for determining the effectiveness of thermal insulation.

SUMMARY OF THE INVENTION

In accordance with the invention, a device is provided for determining the thermal impedance values of insulated barriers and comparing these determined values to those of economic insulation. The device measures the surface temperature of the barrier and comprises a holder and a temperature sensor and indicator means supported on support means slidably mounted in the holder. The holder optionally has provision to attach different reference scales thereon. These reference scales can be provided by using separate overlays or by using an additional slider or the like. Each reference scale has marked thereon a series of R values (resistance of insulation to the flow of heat) and a value or series of values for the temperature difference between inside and outside. The temperature sensor and indicator means encompasses ambient temperatures expected within an area defined by the insulated barrier. The device of the invention provides an inexpensive, easily used means of determining the effectiveness of thermal insulation. The R values determined by the device of the invention can be compared with those suggested for adequate insulation.

BRIEF DESCRIPTION OF THE DRAWING

FIG. 1 depicts, approximately full-size, a thermal insulation effectiveness tester of the invention shown positioned against a surface;

FIG. 2 and 3 depict portions of the thermal insulating effectiveness device of FIG. 1;

DETAILED DESCRIPTION OF THE INVENTION

Figure 4:
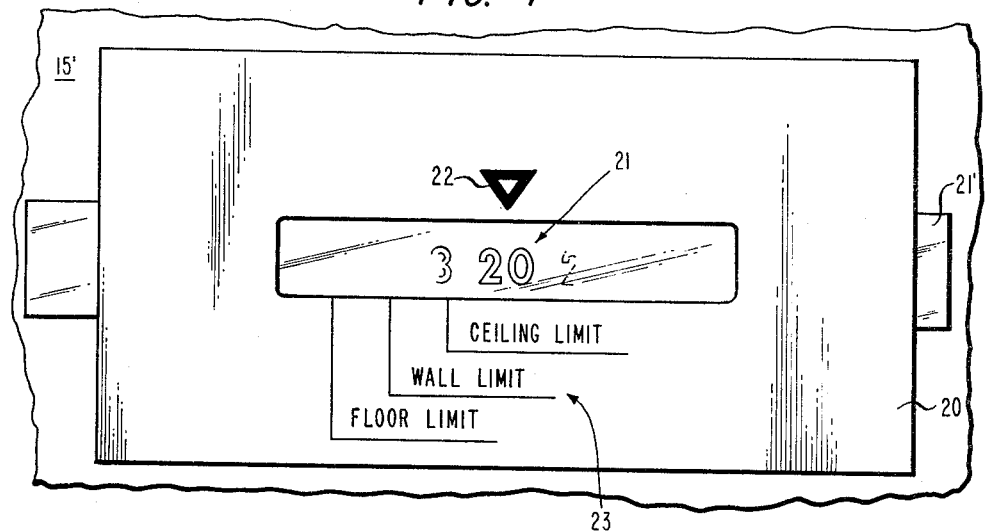
FIG. 4 depicts, approximately full-size, another embodiment of the thermal insulation effectiveness tester of the invention shown positioned against a surface.

Currently in the United States, the prevalent commercial method of specifying the effectiveness of insulation uses an "R-value." This R-value quantifies the resistance of the insulation to the flow of heat; higher R-values describe a greater effectiveness of insulation. The units defining the R-value are given by:

$$R = [Ft^2 - °F. - hr/BTU]. \tag{1}$$

Some insight into the impact of insulation on reducing heat flow can be obtained by considering the following simplified example. Consider a volume of space to be insulated by constructing a cube of length, l, with all six sides having the same value of insulation R. Then the heat flow, H, is given by:

$$H = 6l^2 \Delta T/R = A\Delta T/R \text{ [BTU/hr]}, \tag{2}$$

where $\Delta T$ is the temperature difference between the inside and outside of the cube and A is the total surface area of the cube.

In other words, in order to maintain a temperature difference of $\Delta T$, a quantity of heat equal to H BTU/hr would have to be provided. If the inside were hotter, then H would be added; if the inside were cooler, then H would be removed. Note that the same $\Delta T$ can be maintained for smaller values of H if R is increased.

Determination of the optimum value for R requires an economic analysis. The principal factors include:

(a) The cost of adding or removing units of H by heating or air conditioning (included in this cost is the expense of the fuel or electricity);

(b) The cost of obtaining and installing insulation; and (c) The magnitude of the desirable $\Delta T$ between the inside and outside which, for reasonably comfortable inside temperatures between 65° F. and 82° F., or 18° C. and 28° C., depends on the outside temperature—i.e., on the climatic conditions in the area of the residence.

Maps showing the climatic conditions of the United States in terms of degree-days have been prepared by various government agencies. These maps, together with the other factors (such as, electric and fuel rates) have been previously analyzed by many individuals to determine suggested R values for the walls, floors and ceilings of dwellings in each region of the United States.

The device of the invention measures the temperature of a surface (wall, ceiling, floor) of interest by direct contact. By means of a reference point incorporated in the device, the surface temperature is related to the living space temperature (that space defined by the insulated surfaces), and previously determined optimal performance for insulated structures, e.g., residential. Broadly, the device of the invention comprises a holder and a temperature sensor and indicator means supported on support means slidably mounted in the holder. The holder may additionally include different reference scales attached thereto relating to specific surfaces (wall, floor, ceiling). Use of the device of the invention ordinarily requires knowledge of the outside temperature.

Some insight into the principles by which this device operates can be obtained from the following simplified mathematical model. For a flow of heat, Q, to leave a segment unit area, S, of a typically heated room, the heat flow must pass through two thermal resistances. The first resistance, $R_a$, is the impedance of the boundary layer to the total heat transfer between the interior air temperature at $T_i$ and the barrier surface temperature at $T_s$. The second resistance, R, is the thermal resistance of the barrier itself and includes the contribution of installed insulation. For an outside temperature of $T_o$, the following equation can be written for the flow of heat:

$$Q = S(T_i - T_o)/(R_a + R) = S \Delta T/(R_a + R), \quad (3)$$

where $\Delta T$ is the temperature difference between the interior air temperature and the outside temperature. An additional equation relates this flow of heat to the difference in temperature $\Delta t$, between the interior air temperature $T_i$ and the barrier surface temperature $T_s$ $$Q = S(T_i - T_s)/R_a = S\Delta t/R_a. \quad (4)$$

Simultaneous solution of Eqns. 3 and 4 yields an equation:

$$\Delta t = R_a \Delta T/(R_a + R). \quad (5)$$

This equation can be rewritten in the form:

$$R = R_a(\Delta T - \Delta t)/\Delta t \quad (6)$$

which permits direct determination of R, the thermal resistance of the barrier, if $\Delta t$, $\Delta T$ and $R_a$ are known. The device and procedure of this invention show how to determine $\Delta t$ and $\Delta T$. The values for $R_a$ are available from government publications. Thus, the value of R can be determined. As is shown below, direct determination of this R value is available from the device of the invention.

Measured values for $R_a$ are reported in Housing Research Paper No. 32, April 1954, Housing and Home Finance Agency, Division of Housing Research, Washington, D.C.. That report documents that the total heat transfer across an airspace depends not only on the temperature difference across the airspace and the mean temperature but also on the airspace orientation (e.g., horizontal or vertical) and on the direction of heat flow (e.g., horizontal, up or down). For example, for a given vertical temperature difference across a horizontal airspace, the vertically upward heat flow is greater than the vertically downward heat flow. This requires that $R_a$ have an orientation dependence; that is, difference values of $R_a$ are required to evaluate ceilings, walls, and floors. The tabulation in Table I below, prepared from data taken from Housing Research Paper No. 32, shows the dependence for a 3-inch airspace between surfaces of 0.9 emissivity (typical of construction materials) at mean temperatures of 50° F. and 65° F. with a temperature difference of 10° F. across the airspace.

TABLE I

| Insulated Surface | Orientation of Air Space | Direction of Heat Flow | Mean Temp. °F. | $R_a$ |
|---|---|---|---|---|
| Ceiling | Horizontal | Up | 50 | 0.93 |
|  |  |  | 65 | 0.87 |
| Wall | Vertical | Horizontal | 50 | 1.01 |
|  |  |  | 65 | 0.94 |
| Floor | Horizontal | Down | 50 | 1.22 |
|  |  |  | 65 | 1.13 |

There are several configurations which may be employed in constructing the device of the invention. These are described in detail below. While three devices are described, it will be readily apparent to one skilled in the art that obvious modifications of these may be made. Such modifications are considered to be within the spirit and scope of the invention. Further, while the invention is described in terms of measuring insulation effectiveness against loss of heat in the winter, it is apparent that with simple modifications similar devices may be easily fabricated for use in air conditioned dwellings in the summer.

In one embodiment of the invention, a device is provided for determining the thermal impedance values of insulated barriers and comparing these determined values to those of economic insulation. This device, shown in FIGS. 1, 2, and 3, measures the surface temperature of the barrier and comprises a holder 10 and a temperature sensor and indicater means generally indicated at 11 (FIG. 2) supported on first support means 11' slidably mounted in the holder. The holder has provision to attach different reference scales generally indicated at 12a and 12b (FIG. 3) thereon. These reference scales can be provided by using separate overlays or by using an additional slider 12' (as shown in FIG. 1) or the like. Each reference scale has marked thereon a series of R values (12a) and a series of values (12b) for the temperature difference between inside and outside. The temperature sensor and indicator means encompassses ambient temperatures expected within an area defined by the insulated barrier. The device of the invention provides an inexpensive, easily used means of determining the effectiveness of thermal insulation.

In the preferred embodiment, the temperature and indicator means is a low thermal mass surface reading temperature sensor indicator and means such as a liquid crystal temperature sensor indicator and means. Such a sensor indicator and means comprises a plurality of liquid crystal compositions, which, when exposed to a particular temperature, change color. Thus, the plurality of liquid crystal compositions is arranged sequentially so as to be chromatically responsive to increasing or decreasing temperatures. Strips of liquid crystal temperature sensor and indicator means are readily available over various temperature ranges and form no part of this invention. The temperature range should encompass normally expected ambient temperatures (about 68° F. to 72° F., or about 20° C. to 22° C.), with a range of several degrees on either side.

Thermal impedance values of insulated barriers are determined using the device of FIGS. 1, 2, and 3 as follows:

(a) The temperature difference between the inside and outside of the barrier is determined;

(b) this value 12b is positioned in window 13 of the holder for the reference scale;

(c) the device is held several inches away from a surface 15 whose insulating effectiveness is to be determined;

(d) the temperature sensor and indicator support means 11' is moved until reference point 14 on the holder is substantially aligned with the sensed and indicated temperature;

(e) the device is held against the surface of interest;

(f) any new temperature sensed and indicated is noted, together with its position relative to the R values on the reference scale (looking down vertically from the sensed and indicated temperature value 11 to the R value below). The indicated R value is the insulation effectiveness value.

For example, suppose the difference between inside and outside temperature is 30° C. and that the room temperature is 22° C. If in measuring a wall the indicated temperature is 18° C., then the R value is about 6, as shown in FIG. 1.

The R values determined by this method can be compared with those suggested for economic insulation. One convenient format for presenting the desirable R values uses a map with zones indicated for various insulation effectiveness. Such maps are readily available from vendors of insulation.

The device of FIGS. 1, 2, and 3 is generated by using the following procedure which provides numerical R values and which correctly positions those values onto the device.

(a) A convenient set of $\Delta t$'s is chosen which is broad enough to encompass the expected range and which has fine enough gradations to provide resonable resolution. In the preferred embodiment, these $\Delta t$'s are chosen to be the same as the separations on the liquid crystal temperature sensor indicator and means. For example, with one commercially offered liquid crystal temperature sensor indicator and means having readouts at 2° C. intervals, the preferred $\Delta t$'s are 2°, 4°, 6°, 8°, and 10° C.

(b) A convenient set of $\Delta T$'s is chosen which also is broad enough to encompass the expected range and which has fine enough gradations to provide reasonable resolution. A preferred set of $\Delta T$'s for the case of walls is 10°, 20°, 30°, 40°, and 50° C.

(c) For each combination of $\Delta t$ and $\Delta T$ from the above preferred sets, Equation 6 is used to determine the corresponding value of R. For this purpose, $R_a$ is chosen as 1.0 to generate the R values for walls.

(d) This collection of data is organized into a geometric format with prescribed horizontal spacing. In the preferred embodiment, each horizontal line contains the R values for a particular value of $\Delta T$. The spacing is as follows:

(i) starting from the left, the R value corresponding to $\Delta t$ of 10° C. is entered, (ii) move a distance equal to 2° C. on the liquid crystal temperature sensor indicator and means and enter the R value corresponding to $\Delta t$ of 8° C., (iii) similarly, position and enter the values for $\Delta t$'s of 6°, 4°, and 2° C., (iv) finally, move right a fixed distance and enter the value for $\Delta T$.

A separate horizontal line is generated for each value of $\Delta T$. Table II below presents the concept of this spacing arrangement.

TABLE II

GEOMETRIC FORMAT OF COLLECTED DATA

| $\Delta t$ | | | | | |
|---|---|---|---|---|---|
| 10 | 8 | 6 | 4 | 2 | $\Delta T$ |
| 0 | 0.2 | 0.7 | 1.5 | 4 | 10 |
| 1 | 1.5 | 2.3 | 4 | 9 | 20 |
| 2 | 2.8 | 4 | 6.5 | 14 | 30 |
| 3 | 4 | 5.7 | 9 | 19 | 40 |
| 4 | 5.2 | 7.3 | 12 | 24 | 50 |

(e) An inspection of Table II shows that the R values in vertical columns increases in magnitude for greater $\Delta T$.

(f) Next, each horizontal row is translated sideways to minimize the variability in the R values for the new vertical columns. For example, the horizontal rows are translated to force the R values of 4 into a single vertical column.

(g) Finally, this multirow and translated collection of R values and $\Delta T$ values is compressed into a single row. For each entry, the horizontal position is preserved. R values are entered from the average of that column.

(h) The resulting scale for walls is shown in part of FIG. 3.

(i) Corresponding scales for ceilings and floors can be generated from the wall scale via the following procedure. The values of $R_a$ are different for ceilings, walls and floors. Thus, for fixed $\Delta t$ and R, different values of $\Delta T$ will be generated for ceilings, walls and floors. This can be expressed as:

$$\Delta T' = \Delta T \left( \frac{R_a}{R_a + R} \right) \left( \frac{R_a' + R}{R_a'} \right) \quad (7)$$

where the primed quantities refer to either the ceiling or floor.

(j) The resulting scale is shown in FIG. 3.

(k) The holder in FIG. 1 is ruled and cut to provide a convenient way to correctly associate a stated $\Delta T$ with the appropriate R value for a $\Delta t$.

(l) Because of the approximations used in generating the scales, a $\Delta t$ of at least 2° C. is recommended to provide trustworthy indications of R values.

In a second embodiment, the device and procedure which measures thermal insulation and the suggested values for economic insulation are combined in one device (not shown). In this version, a different reference scale is used for each climatic zone. With this embodiment, the reference scale is marked with a limit point for economic insulation and a series of values for the temperature difference between inside and outside. Use is identical to that described above, except in step (f), where note is made whether a new temperature is sensed and indicated and its position relative to the limit line on the reference scale. During the heating season, if the new sensed and indicated temperature is to the left of the limit point, additional insulation is indicated; if to the right, then the insulation is considered adequate. The reverse considerations would apply during the cooling season.

In yet another embodiment, the device and procedure and the suggested economic R values are combined and used in one device in a different way. There are two components to this device, as shown in FIG. 4. The first component is a low thermal mass surface reading temperature sensor and indicator means generally indicated at 21 supported on support means 21'. In the preferred embodiment this sensor and indicator means again is a liquid crystal temperature sensor and indicator means.

The temperature sensor and indicator support means 21' is slidably mounted in a holder 20. The holder includes means for determining the relationship between the temperature of the living space and that of the insulated surface to be measured. In operation, the strip 21' carrying the temperature sensor and indicator means 21, such as a digital liquid crystal sensor and indicator means, is moved in the holder until the temperature of the heated space is opposite the SET POINT indicator 22 on the holder. Without changing the relative positions of these two elements, the assembly is placed on the surface whose thermal performance is to be determined. The temperature of this surface then causes the liquid crystal display to sense and indicate the temperature of the surface. Because of the low mass and heat capacity of the sensing indicating strip and its rapid response, the temperature of the underlying area is not significantly perturbed. Because of the layout of the serial temperature indications along the sensor and indicator means strip, the temperature difference between the living space and the wall temperature is, therefore, converted to a proportional length of a linear dimension. The scale printed on the holder and indicated generally at 23 then relates the length of this linear dimension to the R-value of the insulated wall structure by means of the expression shown in Equation 6 above.

Figure 5:
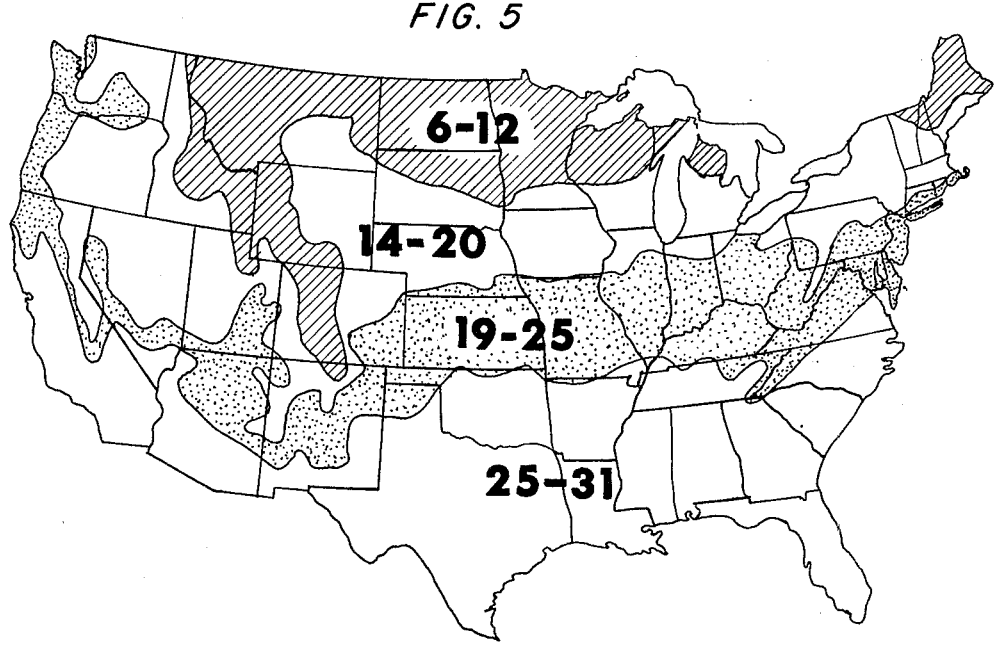
FIG. 5 is a climatic zonal map of the United States of America, depicting temperature ranges (in degrees Fahrenheit) external to insulated surfaces suitable in each zone for use of the device depicted in FIG. 4.

In this device, the air temperature is chosen to be in the relatively narrow range of indoor residential temperature usually maintained at 68° to 72° F. (20° to 22° C.). Because greater insulation is desirable in those regions of outdoor environment where the low temperature is more severe, the outdoor temperature for the test is chosen to ary with the various climatic zones where this device would be used. Such zones for the United States are shown in FIG. 5 and are derived from data in the *National Atlas of the U.S.A.*, U.S. Dept. of the Interior, Geological Survey, Washington, D. C.

The process for using the device depicted in FIG. 4 comprises the following steps:

(a) the climate zone in which the measurement is to be done is determined, employing the map shown in FIG. 5;

(b) at a time when the temperature exterior to the insulated surface lies within that temperature range indicated for the climatic zone and when the temperature interior to the insulated surfaces lies between about 68° F. and 72° F. (or about 20° C. and 22° C.), the device is held several inches away from a surface 15' whose insulating effectiveness is to be determined;

(c) the temperature sensor and indicator support means 21' is moved until the reference point 22 on the holder is substantially aligned with the sensed and indicated temperature.

(d) the device is held against the surface whose insulating effectiveness is being tested; and (e) any new temperature indicated is noted, together with its position relative to the limit point 23 for the surface. If the new sensed and indicated temperature is to the left of the limit point, additional insulation is indicated; if to the right, then the insulation is considered adequate.

The limit points for the various surfaces are determined by comparison with barriers whose thermal impedance is known.

EXAMPLES

EXAMPLE 1

The following readings were taken at a residence located in Zone 19–25 as set forth in FIG. 5, employing a device substantially as shown in FIG. 4. The outside temperature ranged between 21° F. and 24° F.; the inside temperature ranged between 68° F. and 70° F. For many of the surfaces measured, the R value of insulation was known, and thus provided a measure of accuracy of the device.

TABLE III

| Outside Temperature, °F. | Inside Temperature,[1] °F. | Surface Measured | Temperature of Surface (°F.) | Adequate Insulation? | Known R Value[2] |
|---|---|---|---|---|---|
| 24 | 68 | Wall | 64 | Yes | 10 |
| 24 | 70 | Ceiling | 63 | No | 8 |
| 24 | 70 | Ceiling | 66 | Yes | 8 |
| 24 | 70 | Ceiling | 61 | No | 8 |
| 21 | 70 | Wall | 63 | Yes | 10 |
| 21 | 71 | Ceiling | 64 | No | 8 |
| 21 | 71 | Ceiling | 61 | No | 8 |
| 24 | 68 | Floor | 61 | Yes | — |
| 24 | 70 | Wall | 61 | No | 10 |

[1] Temperature measured three inches from surface
[2] Known from building materials and data in Handbook of Engineering Fundamentals

EXAMPLE 2

The following readings were taken at a second residence located in Zone 19–25 as set forth in FIG. 5, employing a device substantially as shown in FIG. 4. The outside temperature was 24° F.; the inside temperature, measured three inches from the surface being tested, ranged from 21° to 24° C. For many of the surfaces measured, the R value of insulation was known, and, again, provided a measure of accuracy of the device.

TABLE IV

| Outside Temperature, °F. | Inside Temperature,[1] °C. | Surface Measured | Temperature of Surface (°C.) | Adequate Insulation Indicated | Known R Value[2] |
|---|---|---|---|---|---|
| 24 | 22 | Wall | 20 | Yes | 12.9 |
|  | 22 | Wall | 21 | Yes | 12.9 |
|  | 23 | Wall | 21 | Yes | 12.9 |

TABLE IV-continued

| Outside Temperature, °F. | Inside Temperature,[1] °C. | Surface Measured | Temperature of Surface (°C.) | Adequate Insulation Indicated | Known R Value[2] |
|---|---|---|---|---|---|
| | 24 | Ceiling | 23 | Yes | 20.0 |
| | 21 | Floor | 20 | Yes | 21.2 |
| | 23 | Wall | 22 | Yes | 12.4 |
| | 22 | Ceiling | 20 | Yes | 20.0 |
| | 20 | Floor | 19 | Yes | 21.4 |

[1] Temperature measured three inches from surface.
[2] Known from building materials and data in Handbook of Engineering Fundamentals.

We claim:

1. A device for determining thermal impedance values, expressed in units of effectiveness of insulation, of interior surfaces defining a living space which comprises:
   (a) a holder, having marked thereon a first reference point and a second reference point;
   (b) a temperature sensing and indicating means supported on first support means slidably mounted in said holder, said temperature sensing and indicating means encompassing ambient temperatures within the living space defined by said interior surfaces;
   (c) a first means in said holder for exposing a portion of said temperature sensing and indicating means, said first exposing means adjacent said first reference point;
   (d) a reference scale supported on second support means slidably mounted in said holder, said reference scale having marked thereon
      (1) a series of values of temperature difference, and
      (2) a series of R values;
   (e) a second means in said holder for exposing a portion of said temperature difference values, said second exposing means adjacent said second reference point; and
   (f) a third means in said holder for exposing a portion of said R values,
said temperature sensing and indicating means, said reference scale with said R values and temperature difference values marked thereon and said reference points positioned such that upon (i) determining the temperature difference on both the interior and exterior side of a surface, (ii) setting inside temperature against said first reference point and (iii) holding said device against said surface to generate its temperature value, then the R value of said surface is substantially aligned with the indicated interior surface temperature value.

2. The device of claim 1 in which said temperature sensing and indicating means comprises a plurality of temperature gradations, each gradation comprising a liquid crystal composition chromatically responsive to a particular temperature.

3. A device for determining thermal impedance values of interior surfaces defining a living space and comparing said values obtained to those of economically attractive insulation which comprises:
   (a) a holder, having marked thereon a reference point and minimum limit points corresponding to walls, ceilings and floors, said limit points marking indications of minimum insulation acceptable for walls, ceilings and floors, respectively, relative to said reference point;
   (b) a temperature sensing and indicating means supported on support means freely slidably mounted in said holder, said temperature sensing and indicating means encompassing ambient temperatures expected within the region defined by said interior surfaces; and
   (c) a window in said holder for exposing a portion of said temperature sensing and indicating means, said window adjacent said reference point and said minimum limit points,
said temperature sensing and indicating means, said reference point and said limit points in spaced relationship such that the adequacy of insulation of said interior surfaces may be determined from a knowledge of the temperature on both sides of an interior surface and at some distance from the interior side of the surface.

4. The device of claim 3 in which said temperature sensing and indicating means comprises a plurality of temperature gradations, each gradation comprising a liquid crystal composition chromatically responsive to a particular temperature.

5. A device for determining thermal impedance values, expressed in units of effectiveness of insulation known as R values, of interior surfaces defining a living space which comprises:
   (a) a holder, having marked thereon a first reference point and a second reference point;
   (b) a temperature sensing and indicating means supported on first support means slidably mounted in said holder, said temperature sensing and indicating means encompassing ambient temperatures expected within the region defined by said interior surfaces;
   (c) a first window in said holder for exposing a portion of said temperature sensing and indicating means, said first window adjacent said first reference point; and
   (d) a reference scale supported on second support means slidably mounted in said holder, said reference scale having marked thereon
      (1) a series of values of temperature difference between an interior surface and the outside related to walls, ceilings and floors, with a second window in said holder for exposing a portion of said temperature difference values adjacent said second reference point, and
      (2) a series of R values, with a third window in said holder for exposing a portion of said R values,
said temperature sensing and indicating means, said reference scale and said R values and temperature difference values marked thereon and said reference points positioned such that upon (i) determining temperature difference for a particular surface, (ii) setting inside temperature against said first reference point and (iii) holding said device against said particular interior surface to generate its temperature value, then the R value of said surface is substantially aligned with the sensed and indicated interior surface temperature value.

6. The device of claim 5 in which said temperature sensing and indicating means comprises a plurality of temperature gradations, each gradation comprising a liquid crystal composition chromatically responsive to a particular temperature.

* * * * *